United States Patent
Klaas

(10) Patent No.: US 9,217,699 B2
(45) Date of Patent: Dec. 22, 2015

(54) METHOD AND A DEVICE FOR THE REPRODUCTION OF AN IMPACT EVENT

(75) Inventor: Andrej Klaas, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 319 days.

(21) Appl. No.: 13/606,250

(22) Filed: Sep. 7, 2012

(65) Prior Publication Data

US 2013/0061654 A1    Mar. 14, 2013

Related U.S. Application Data

(60) Provisional application No. 61/532,128, filed on Sep. 8, 2011.

(30) Foreign Application Priority Data

Sep. 8, 2011 (DE) .......................... 10 2011 082 373

(51) Int. Cl.
| | |
|---|---|
| *G01N 3/317* | (2006.01) |
| *G01N 3/303* | (2006.01) |
| *G01N 3/30* | (2006.01) |
| *G01N 3/06* | (2006.01) |
| *G01N 3/52* | (2006.01) |
| *G01N 3/36* | (2006.01) |

(52) U.S. Cl.
CPC *G01N 3/317* (2013.01); *G01N 3/06* (2013.01); *G01N 3/30* (2013.01); *G01N 3/303* (2013.01); *G01N 3/36* (2013.01); *G01N 3/52* (2013.01)

(58) Field of Classification Search
CPC ......... G01N 3/317; G01N 3/303; G01N 3/36; G01N 3/30; G01N 3/52; G01N 3/06
USPC ....................... 73/12.04, 12.05, 12.11; 702/41
See application file for complete search history.

(56) References Cited

U.S. PATENT DOCUMENTS

| | | | | |
|---|---|---|---|---|
| 3,426,578 A * | 2/1969 | Bergs | ...................... | G01N 3/303 73/12.06 |
| 3,597,969 A * | 8/1971 | Curchack | ................ | F42B 35/00 73/12.05 |
| 3,792,354 A * | 2/1974 | Slaght | ..................... | G04F 10/04 324/178 |
| 3,823,600 A * | 7/1974 | Wolff | ...................... | G01N 3/307 73/12.07 |
| 3,879,982 A * | 4/1975 | Schmidt | .................... | G01N 3/48 73/12.01 |
| 4,640,120 A * | 2/1987 | Garritano | ................ | G01N 3/303 73/12.13 |
| 4,649,735 A * | 3/1987 | Pihlaja | .................... | G01N 3/303 73/12.12 |
| 4,696,182 A * | 9/1987 | Meir | ....................... | G01N 3/307 73/12.05 |
| 4,699,000 A * | 10/1987 | Lashmore | ................ | G01N 3/42 73/794 |
| 5,184,499 A * | 2/1993 | Oppliger | ................. | F41B 11/00 73/11.01 |
| 5,485,758 A * | 1/1996 | Brown | .............. | G01M 17/0078 73/12.04 |
| 5,714,675 A * | 2/1998 | Yoshida | .................. | G01M 7/08 73/12.04 |
| 5,739,411 A * | 4/1998 | Lee | ........................... | G01N 3/48 73/12.09 |

(Continued)

FOREIGN PATENT DOCUMENTS

| | | |
|---|---|---|
| EP | 1 061 354 B1 | 5/2007 |
| EP | 1 553 393 B1 | 8/2009 |

*Primary Examiner* — Lisa Caputo
*Assistant Examiner* — Tran M Tran
(74) *Attorney, Agent, or Firm* — Greer, Burns & Crain, Ltd.

(57) ABSTRACT

A method and a device for the execution of the method for the reproduction of an impact event of a projectile, with any ratio of energy and impulse, wherein a feed rate of an impress element is controlled by taking account of an alteration in velocity that is proportional to the quotient of a resistance force and a freely selected projective mass.

6 Claims, 1 Drawing Sheet

(56) References Cited

U.S. PATENT DOCUMENTS

| | | | | |
|---|---|---|---|---|
| 6,202,496 B1* | 3/2001 | Jakob | G01N 3/40 | 73/12.12 |
| 6,257,352 B1* | 7/2001 | Nelson | B28D 1/26 | 173/211 |
| 6,523,391 B1* | 2/2003 | Knox | G01M 7/08 | 73/12.01 |
| 6,769,287 B2* | 8/2004 | Stewart | F41B 7/00 | 124/20.1 |
| 7,412,870 B2* | 8/2008 | Brankov | G01N 3/303 | 73/12.11 |
| 7,430,892 B2* | 10/2008 | McNamara | G01N 3/48 | 73/12.13 |
| 7,886,574 B2* | 2/2011 | Kaneko | G01N 3/30 | 73/12.01 |
| 8,261,620 B2* | 9/2012 | Brandestini | G01N 3/307 | 73/803 |
| 8,408,042 B2* | 4/2013 | Perrier | G01M 7/08 | 73/12.01 |
| 8,548,752 B2* | 10/2013 | Matlschweiger | G01M 7/08 | 702/41 |
| 8,561,475 B2* | 10/2013 | Johnson | G01N 3/08 | 73/826 |
| 2002/0056558 A1* | 5/2002 | Bongers-Ambrosius | B25D 11/12 | 173/201 |
| 2004/0134263 A1* | 7/2004 | Tsujii | G01N 3/42 | 73/81 |
| 2005/0188744 A1* | 9/2005 | Camio | G01M 7/08 | 73/12.01 |
| 2007/0266764 A1* | 11/2007 | Goyal | G01N 3/303 | 73/12.09 |
| 2008/0282783 A1* | 11/2008 | Valleggi | G01N 3/36 | 73/82 |
| 2011/0146376 A1* | 6/2011 | Subert | E02D 1/02 | 73/12.06 |
| 2013/0333442 A1* | 12/2013 | Kibat | G01L 1/247 | 73/12.09 |

* cited by examiner

METHOD AND A DEVICE FOR THE REPRODUCTION OF AN IMPACT EVENT

This application claims priority to German Patent Application No. 10 2011 082 373.5 filed Sep. 8, 2011, and claims the benefit to U.S. Provisional Application No. 61/532,128, filed Sep. 8, 2011, the entire contents of each of which are hereby incorporated by reference.

The invention concerns a method for the reproduction of an impact event for a projectile, and a device for the execution of such a method.

For purposes of designing an aircraft structure with structural elements such as fuselage shells, longitudinal or transverse stiffeners, ribs and similar, instances of damage are regularly introduced into the structural elements by means of impact events, in the context of structural testing. The instances of damage caused by impact events are dependent both on the impact energy and also on the impulse at the point of impact. Thus, for example, a light, fast, free projectile causes a different incidence of damage from that of a heavy, slow projectile with the same energy. Therefore impact scenarios such as, for example, a falling tool or a vehicle collision, are typically defined, and represented with appropriate devices. Devices are often used in which a free projectile with a particular mass impacts onto a structural element to be tested, i.e. the test piece, with a defined velocity. The acceleration of the projectile is achieved, for example, by gravitation, air pressure, an electrical linear drive, or by a spring force. The projectile is usually guided by means of a suitable retaining device such as rails, tubes, and similar, as a result of which the projectile is braked in an undesired manner. While it is true that an energy:impulse ratio can be represented by varying the projectile mass, the weight of the projectiles cannot be reduced arbitrarily because of geometrical limitations. Thus the projectiles must carry retaining, releasing and measuring devices, and must have a minimum strength. A maximum projectile mass is prescribed by the dimensions of the device. Moreover the manufacture of the projectiles is cost intensive.

Alternatively devices are used which enable a loading controlled in terms of force or the path traversed by means of an impress element guided by a slow actuator. In these devices the energy is determined from the measurement of force and track distance by means of integration. However, this type of loading corresponds to an impact with an infinite impulse, i.e. with an infinite mass.

The object of the invention is to create a method for the reproduction of an impact event of a projectile, which removes the above-cited disadvantages and enables the adjustment of any ratio of energy and impulse, and also a device for the execution of such a method.

This object is achieved by means of a method with the features of Claim 1, and by means of a device with the features of Claim 3.

In an inventive method for the reproduction of an impact event of a projectile, a feed rate of an impress element is controlled by taking account of an alteration in velocity that is proportional to the quotient of a resistance force and a freely selected projectile mass.

The inventive method enables a simulation of a free body movement of a projectile with any ratio of energy and impulse. By the simulation of the free body movement and the measurement of the resistance force of the test piece a characteristic is inventively represented that corresponds to the action of the free projectile. Here, moreover, by taking account of the resistance force, impact energy losses such as occur in a device of known art with projectile guides are eliminated. Since the projectile mass can be freely selected any impulse can be represented up to the extreme case of an infinite impulse (no reduction of the feed rate). A lower limit for the impulse (corresponding to a minimum projectile mass that can be implemented) is determined only by the maximum feed rate.

A test piece is preferably firstly positioned relative to the impress element. The impress element is then traversed with the feed rate in the direction of the test piece. When the impress element impinges on the test piece the resistance force of the test piece is then measured. Next an alteration in velocity is determined. The feed rate is then reduced in accordance with the alteration in velocity.

An inventive device for the execution of a method to reproduce an impact event of a projectile, in particular for the execution of the inventive method, has an impress element for purposes of introducing the impact event, an actuator for purposes of traversing the impress element with a feed rate in the direction of a test piece, a force measurement device for purposes of measuring a resistance force of the test piece, and a control device for purposes of determining an alteration in velocity that is proportional to the quotient of the resistance force and the mass, and for purposes of reducing the feed rate by the alteration in velocity.

Such a device allows the simulation of a free body movement of a projectile with any ratio of energy and impulse. Moreover the device is compact and can thus be embodied so as to be mobile.

The actuator is preferably controlled in terms of the path traversed and has a response characteristic that corresponds to a characteristic of a projectile in a free body movement. The actuator is thus very fast, a fact that enables an accurate simulation of the damage event.

In a technically simple example of embodiment the actuator is driven pneumatically.

In an alternative example of embodiment the actuator is driven hydraulically. A hydraulic actuator allows a fine adjustment of the feed rate and thus very accurate reproduction of the impact event.

In a further example of embodiment the actuator is driven electromechanically. An electromechanical actuator allows a very fine adjustment of the feed rate. Moreover such a device is highly flexible, since pneumatic or hydraulic connections are not required to operate the actuator; just an electrical power source is to be made available. Furthermore an electromechanical actuator has reduced complexity and low maintenance compared with a pneumatic or an hydraulic variant.

The force measurement device is preferably integrated into the impress element, so that the resistance force of the test piece can be recorded directly.

Other advantageous examples of embodiment of the invention are the subject of further subsidiary claims.

In what follows preferred examples of embodiment of the invention are elucidated in more detail with the aid of schematic representations. Here:

Figure 1:
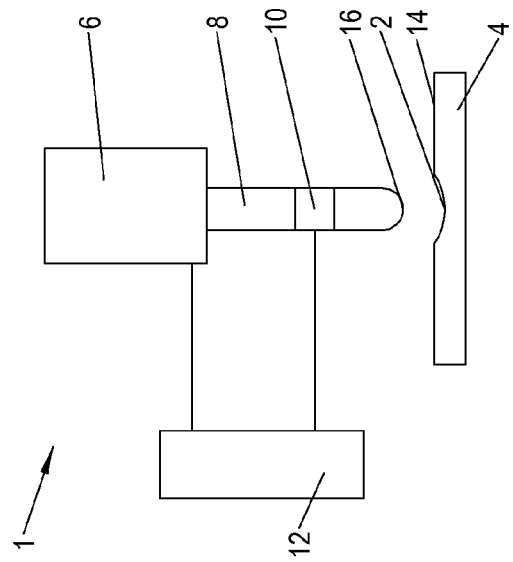
FIG. 1 shows a schematic test rig with an inventive device for the reproduction of an impact event of a projectile.

In accordance with FIG. 1 an inventive device 1 for the reproduction of an impact event of a projectile, i.e. for the introduction of an incidence of damage 2 (see FIG. 2) into a test piece 4 by the simulation of a free body movement of a projectile with any ratio of energy and impulse, an actuator 6, an impress element 8, a force measurement device 10, and also a control device 12.

The actuator 6 is controlled in terms of the path traversed and has a response characteristic that corresponds to a characteristic of a projectile in a free body movement, and thus allows a simulation of a free body movement. It serves to extend the impress element 8 with a feed rate in the direction of the test piece 4 and by virtue of its short response characteristic is very fast. It is preferably provided with an electromechanical drive.

The impress element 8 is configured in the shape of a rod, with a foot section and a head section. The foot section is guided in the actuator 6. The head section is pressed against a surface 14 of the test piece 4, and to this end has a contact surface 16 in the form of a shell, i.e. a hemisphere.

The force measurement device 10 is integrated into the impress element 8 or is connected to the latter. It serves to measure a resistance force of the test piece 4 when the impress element 8 impinges on the test piece 4, and as the impress element is impressed into the test piece 4.

The control device 12 serves to control the feed rate of the impress element 8. To this end the control device 12 has a first system to determine an alteration of velocity that is proportional to the quotient of the resistance force and the mass of the projectile whose impact effect is to be simulated. In addition the control device 12 has a second system to reduce the feed rate in accordance with the alteration in velocity.

Figure 2:
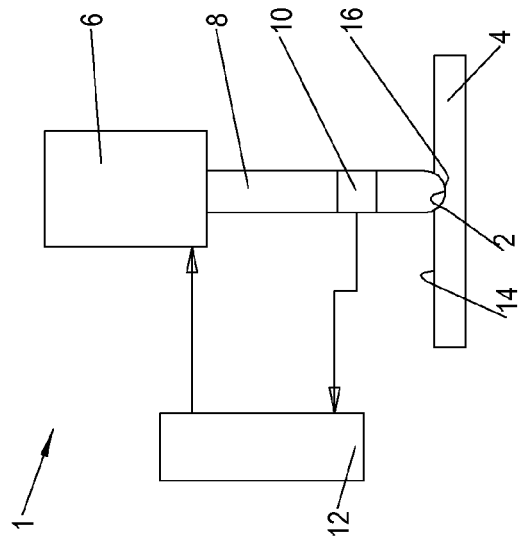
FIG. 2 shows the introduction of an incidence of damage into the test piece.
Figure 3:
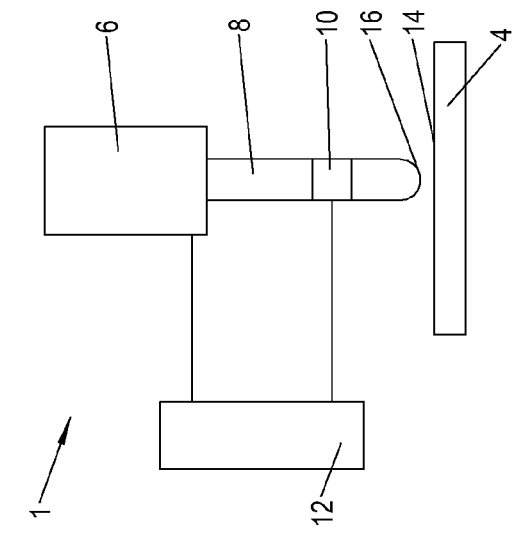
FIG. 3 shows the test rig from FIG. 1 after the reproduction of the impact event.

In what follows a preferred method for the simulation of a free body movement of a projectile with any ratio of energy and impulse is explained with the aid of FIGS. 1, 2 and 3. As shown in FIG. 1, the test piece 4 is aligned orthogonally relative to the impress element 8. The device 1 is located in its base position and the impress element 8 is retracted. The actuator 6 is then activated and the impress element 8 is extended in the direction of the test piece 4 with a defined feed rate. When the impress element 8 impinges on the test piece 4 it penetrates into the test piece 4, as shown in FIG. 2, and forms an incidence of damage 2. As it penetrates into the test piece 4 the impress element 8 is braked as a function of a resistance force of the test piece 4 and the selected projectile mass. The impingement of the impress element 8 on the surface 14 of the test piece 4 is recorded by the force measurement device 10 in the form of the resistance force of the test piece 4. The force measurement device 10 signals the resistance force to the control device 12, which in a first step determines an alteration in velocity of the impress element 8 that is proportional to the quotient of the resistance force and the mass. In a second step the control device 12 reduces the feed rate in accordance with the alteration in velocity. Thus in the case of a large alteration in velocity the impress element 8 is quickly braked. However, in the case of a small alteration in velocity the impress element 8 is slowly braked. In principle in the case of a hard test piece 4 with the same mass the alteration in velocity is greater than in the case of a soft test piece.

After the impress element 8 has been fully braked the device 1 is transferred back into its base position. To this end the actuator 6 is activated such that the impress element 8 is retracted. As a result an incidence of damage 2 is introduced into the test piece 4 by a guided impress element 8, which corresponds to an incidence of damage caused by a free projectile with a particular impact energy and a particular impact impulse. In the example of embodiment shown the incidence of damage 2 is represented as a plastic deformation of the test piece 4. Any elastic deformation of the test piece 4 is not indicated for reasons of clarity. However, it should be mentioned that elastic deformations of the test piece 4 are also accounted for by the method, i.e. the method also functions in the case of a purely elastic deformation of the test piece 4.

Since the projectile mass can be freely selected, any impulse up to the extreme case of the infinite impulse (no alteration of the feed rate) can be represented. A lower limit for the impulse (corresponding to a minimum projectile mass that can be implemented) is determined only by the maximum feed rate.

Disclosed is a method for the reproduction of an impact event of a projectile, with any ratio of energy and impulse, wherein a feed rate of an impress element is controlled by taking account of an alteration in velocity that is proportional to the quotient of a resistance force and a freely selected projectile mass; also disclosed is a device for the execution of the method.

REFERENCE SYMBOL LIST

1 Device
2 Incidence of damage
4 Test piece
6 Actuator
8 Impress element
10 Force measurement device
12 Control device
14 Surface
16 Contact surface

The invention claimed is:

1. A method for reproduction of an impact event of a projectile, comprising the steps of: positioning a test piece relative to an impress element, extending the impress element with an advance velocity in the direction of the test piece to introduce the impact event on a surface of the test piece, measuring a resistance force of the test piece when the impress element impinges on the surface of the test piece, determining a variation in velocity of the impress element, wherein the variation in velocity is proportional to the quotient of the resistance force and any freely selectable projectile mass, and thereafter reducing the advance velocity of the impress element according to the determined variation in velocity of said impress element, said variation being proportional to the quotient of the resistance force and any projectile mass; reducing a feed rate of the impress element in accordance with an alteration of the velocity of said impress element, such that the impress element is actively braked to match the impulse experienced by the projectile in order to simulate the impact of different projectiles having different masses.

2. A device for execution of a method for reproduction of an impact event of a projectile, comprising: an impress element to introduce the impact event on a surface of a test piece, an actuator to guide and extend the impress element in the direction of the test piece with an advance velocity, a force measurement device to measure a resistance force of the test piece when the impress element impinges on the surface of the test piece, and a control device configured to determine a variation in velocity of the impress element, wherein the variation in velocity is proportional to the quotient of the resistance force and any freely selectable projectile mass, the control device being further configured and to reduce the advance velocity of the impress element according to the determined variation in velocity of said impress element, said variation being proportional to the quotient of the resistance force and any projectile mass; wherein the control device is configured to reduce a feed rate of the impress element in accordance with an alteration of the velocity of said impress element, such that the impress element is actively braked to match the impulse experience by the projectile in order to simulate the impact of different projectiles having different masses.

3. The device in accordance with claim 2, wherein the actuator is driven pneumatically.

4. The device in accordance with claim 2, wherein the actuator is driven hydraulically.

5. The device in accordance with claim 2, wherein the actuator is driven electromechanically.

6. The device in accordance with claim 2, wherein the force measurement device is integrated into the impress element.

\* \* \* \* \*